United States Patent
Villiers et al.

(10) Patent No.: US 7,575,599 B2
(45) Date of Patent: *Aug. 18, 2009

(54) INTERVERTEBRAL PROSTHETIC DISC WITH METALLIC CORE

(75) Inventors: Malan de Villiers, Irene (ZA); Ulrich Hahnle, Saxonwold (ZA); David Hovda, Mountain View, CA (US)

(73) Assignee: SpinalMotion, Inc., Mountain View, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 10/903,913

(22) Filed: Jul. 30, 2004

(65) Prior Publication Data

US 2006/0025862 A1   Feb. 2, 2006

(51) Int. Cl.
*A61F 2/44* (2006.01)

(52) U.S. Cl. .................. 623/17.14; 623/17.15

(58) Field of Classification Search ... 623/17.11–17.16, 623/18.11; 606/61
See application file for complete search history.

(56) References Cited

U.S. PATENT DOCUMENTS

| | | | |
|---|---|---|---|
| 3,486,505 A | 12/1969 | Morrison | |
| 4,759,766 A * | 7/1988 | Buettner-Janz et al. | .. 623/17.15 |
| 4,759,769 A | 7/1988 | Hedman et al. | |
| 4,834,757 A | 5/1989 | Brantigan | |
| 4,863,477 A | 9/1989 | Monson | |
| 4,997,432 A | 3/1991 | Keller | |
| 5,035,716 A | 7/1991 | Downey | |
| 5,071,437 A | 12/1991 | Steffee | |
| 5,122,130 A | 6/1992 | Keller | |
| 5,195,526 A | 3/1993 | Michelson | |
| 5,258,031 A | 11/1993 | Salib et al. | |
| 5,314,477 A | 5/1994 | Marnay | |
| 5,370,697 A | 12/1994 | Baumgartner | |
| 5,401,269 A * | 3/1995 | Buttner-Janz et al. | .... 623/17.15 |

(Continued)

FOREIGN PATENT DOCUMENTS

EP   0333990 A2   9/1989

(Continued)

OTHER PUBLICATIONS

U.S. Appl. No. 60/546,027, filed Feb. 19, 2004 to Zubok, 21 pages total.

(Continued)

*Primary Examiner*—Pedro Philogene
(74) *Attorney, Agent, or Firm*—Townsend and Townsend and Crew LLP

(57) ABSTRACT

A prosthetic disc for insertion between adjacent vertebrae includes a core having upper and lower curved surfaces and upper and lower plates. At least one of the curved surfaces of the core is metallic, and in some embodiments the entire core is metallic. Each plate has an outer surface which engages a vertebra and a metallic inner curved surface which is shaped to slide over one of the curved surfaces of the core. In some embodiments, the center of rotation of the core is free to move relative to the upper and lower metallic plates. In some embodiments, one or more channels extend across one or both of the curved surfaces of the core for allowing passage of bodily fluid to promote lubrication between the core and at least one of the plates.

64 Claims, 4 Drawing Sheets

U.S. PATENT DOCUMENTS

| | | | |
|---|---|---|---|
| 5,415,704 A | 5/1995 | Davidson | |
| 5,507,816 A | 4/1996 | Bullivant | |
| 5,534,030 A | 7/1996 | Navarro et al. | |
| 5,556,431 A * | 9/1996 | Buttner-Janz | 623/17.15 |
| 5,674,296 A | 10/1997 | Bryan et al. | |
| 5,676,701 A | 10/1997 | Yuan et al. | |
| 5,676,702 A | 10/1997 | Ratron | |
| 5,702,450 A | 12/1997 | Bisserie | |
| 5,797,909 A | 8/1998 | Michelson | |
| 5,824,094 A | 10/1998 | Serhan et al. | |
| 5,865,846 A | 2/1999 | Bryan et al. | |
| 5,888,226 A * | 3/1999 | Rogozinski | 623/17.16 |
| 5,899,901 A | 5/1999 | Middleton | |
| 5,899,911 A | 5/1999 | Carter | |
| 5,989,291 A | 11/1999 | Ralph et al. | |
| 6,001,130 A | 12/1999 | Bryan et al. | |
| 6,019,792 A | 2/2000 | Cauthen | |
| 6,022,376 A | 2/2000 | Assell et al. | |
| 6,039,763 A | 3/2000 | Shelokov | |
| 6,096,038 A | 8/2000 | Michelson | |
| 6,139,579 A | 10/2000 | Steffee et al. | |
| 6,146,421 A | 11/2000 | Gordon et al. | |
| 6,156,067 A * | 12/2000 | Bryan et al. | 623/17.15 |
| 6,162,252 A | 12/2000 | Kuras et al. | |
| 6,235,030 B1 | 5/2001 | Zuckerman et al. | |
| 6,261,296 B1 | 7/2001 | Aebi et al. | |
| 6,315,797 B1 | 11/2001 | Middleton | |
| 6,348,071 B1 | 2/2002 | Steffee et al. | |
| 6,368,350 B1 | 4/2002 | Erickson et al. | |
| 6,416,551 B1 | 7/2002 | Keller | |
| 6,447,544 B1 | 9/2002 | Michelson | |
| 6,478,800 B1 | 11/2002 | Fraser et al. | |
| 6,517,580 B1 | 2/2003 | Ramadan et al. | |
| 6,520,996 B1 | 2/2003 | Manasas et al. | |
| 6,527,804 B1 | 3/2003 | Gauchet et al. | |
| 6,562,047 B2 | 5/2003 | Ralph et al. | |
| 6,582,466 B1 | 6/2003 | Gauchet | |
| 6,592,624 B1 | 7/2003 | Fraser et al. | |
| 6,599,294 B2 | 7/2003 | Fuss et al. | |
| 6,607,558 B2 | 8/2003 | Kuras | |
| 6,610,092 B2 | 8/2003 | Ralph et al. | |
| 6,645,248 B2 | 11/2003 | Casutt | |
| 6,652,533 B2 | 11/2003 | O'Neil | |
| 6,666,866 B2 | 12/2003 | Mertz et al. | |
| 6,669,732 B2 | 12/2003 | Serhan et al. | |
| 6,682,562 B2 | 1/2004 | Viart et al. | |
| 6,689,132 B2 | 2/2004 | Biscup | |
| 6,706,068 B2 | 3/2004 | Ferree | |
| 6,712,825 B2 | 3/2004 | Aebi et al. | |
| 6,726,720 B2 | 4/2004 | Ross et al. | |
| 6,740,118 B2 | 5/2004 | Eisermann et al. | |
| 6,770,095 B2 | 8/2004 | Grinberg et al. | |
| 6,814,737 B2 | 11/2004 | Cauthen | |
| 6,875,213 B2 | 4/2005 | Michelson | |
| 6,963,071 B2 | 11/2005 | Bristol | |
| 6,966,929 B2 | 11/2005 | Mitchell | |
| 6,994,727 B2 | 2/2006 | Khandkar et al. | |
| 7,025,787 B2 * | 4/2006 | Bryan et al. | 623/17.16 |
| 7,056,344 B2 | 6/2006 | Huppert et al. | |
| 7,179,294 B2 * | 2/2007 | Eisermann et al. | 623/17.15 |
| 7,182,784 B2 * | 2/2007 | Evans et al. | 623/17.15 |
| 7,270,679 B2 * | 9/2007 | Istephanous et al. | 623/17.11 |
| 7,331,995 B2 * | 2/2008 | Eisermann et al. | 623/17.14 |
| 2001/0016773 A1 | 8/2001 | Serhan et al. | |
| 2001/0029377 A1 | 10/2001 | Aebi et al. | |
| 2002/0035400 A1 | 3/2002 | Bryan et al. | |
| 2002/0045904 A1 | 4/2002 | Fuss et al. | |
| 2002/0128715 A1 | 9/2002 | Bryan et al. | |
| 2002/0198532 A1 | 12/2002 | Michelson | |
| 2003/0009224 A1 | 1/2003 | Kuras | |
| 2003/0074076 A1 | 4/2003 | Ferree et al. | |
| 2003/0100951 A1 | 5/2003 | Serhan et al. | |
| 2003/0135277 A1 | 7/2003 | Bryan et al. | |
| 2003/0191536 A1 | 10/2003 | Ferree | |
| 2003/0199982 A1 | 10/2003 | Bryan | |
| 2003/0204261 A1 | 10/2003 | Eisermann et al. | |
| 2003/0208271 A1 | 11/2003 | Kuras | |
| 2004/0002761 A1 | 1/2004 | Rogers et al. | |
| 2004/0024407 A1 | 2/2004 | Ralph | |
| 2004/0030391 A1 | 2/2004 | Ferree | |
| 2004/0073312 A1 | 4/2004 | Eisermann et al. | |
| 2004/0143270 A1 | 7/2004 | Zucherman et al. | |
| 2004/0176843 A1 | 9/2004 | Zubok et al. | |
| 2005/0021145 A1 | 1/2005 | de Villiers et al. | |
| 2005/0021146 A1 | 1/2005 | de Villiers et al. | |
| 2005/0043800 A1 | 2/2005 | Paul et al. | |
| 2005/0085917 A1 | 4/2005 | Marmay et al. | |
| 2005/0107881 A1 | 5/2005 | Alleyne et al. | |
| 2005/0149189 A1 | 7/2005 | Mokhtar et al. | |
| 2005/0192586 A1 | 9/2005 | Zuckerman et al. | |
| 2005/0192670 A1 | 9/2005 | Zubok et al. | |
| 2005/0197706 A1 | 9/2005 | Hovorka et al. | |
| 2005/0251262 A1 | 11/2005 | de Villiers et al. | |
| 2005/0261772 A1 | 11/2005 | Filippi et al. | |
| 2005/0267580 A1 | 12/2005 | Suddaby | |
| 2006/0004453 A1* | 1/2006 | Bartish et al. | 623/17.15 |
| 2006/0025862 A1 | 2/2006 | de Villiers et al. | |
| 2006/0036325 A1 | 2/2006 | Paul et al. | |
| 2006/0041313 A1 | 2/2006 | Allard et al. | |
| 2006/0069439 A1 | 3/2006 | Zucherman et al. | |
| 2006/0293754 A1 | 12/2006 | de Villiers et al. | |
| 2007/0061011 A1 | 3/2007 | de Villiers et al. | |

FOREIGN PATENT DOCUMENTS

| | | |
|---|---|---|
| EP | 0560140 A1 | 9/1993 |
| EP | 0560141 A1 | 9/1993 |
| EP | 591712 A1 | 4/1994 |
| EP | 1142544 A1 | 10/2001 |
| EP | 1153582 A2 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| WO | WO 00/35384 | 6/2000 |
| WO | WO 01/01893 A1 | 1/2001 |
| WO | 2004026187 A1 | 4/2004 |
| WO | 2005053580 A1 | 6/2005 |
| WO | WO 2005/053580 A1 | 6/2005 |
| ZA | 2003/9312 | 11/2003 |

OTHER PUBLICATIONS

Hellier, et al., "Wear Studies for Development of an Intervertebral Disc Prosthesis," Spine, (1992) vol. 17 (6), Supplement pp. 86-96.
Karin Buttner-Janz, The Development of the Artificial Disc, Introduction, 1989, pp. 1-18, Library of Congress Catalogue No. 92-75582, ISBN 0-9635430-0-8.
PCT International Search Report.
International Search Report PCT/US05/26160 Jul. 21, 2005.

* cited by examiner

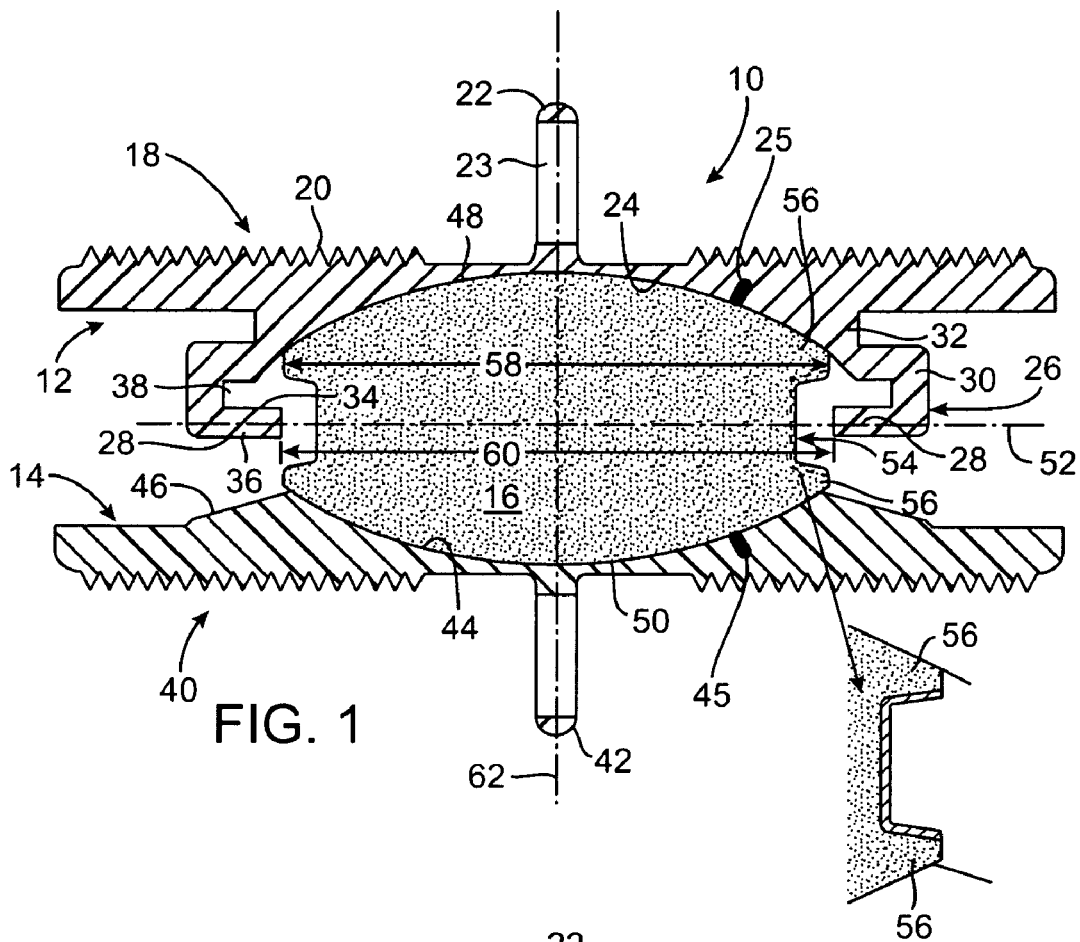
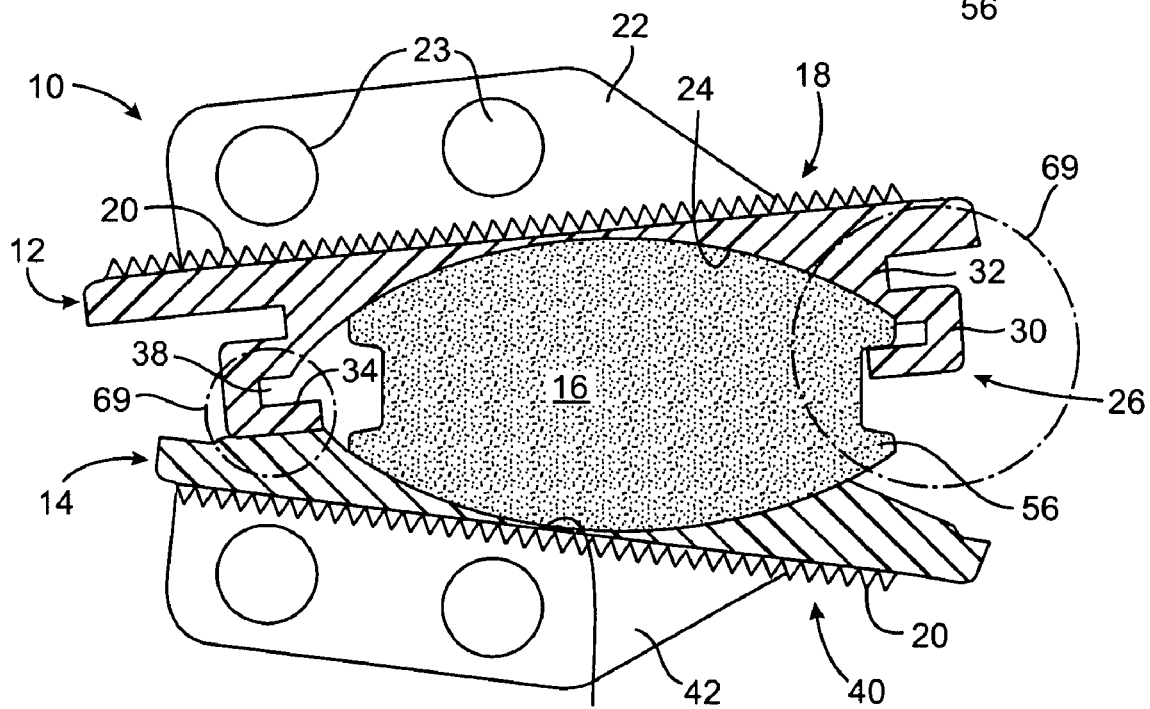

INTERVERTEBRAL PROSTHETIC DISC WITH METALLIC CORE

CROSS-REFERENCES TO RELATED APPLICATIONS

This application is related to U.S. patent application Ser. Nos. 10/855,253 and 10/855,817, both of which were filed on May 26, 2004, and both of which are hereby incorporated fully by reference.

BACKGROUND OF THE INVENTION

1. Field of the Invention

This invention relates to medical devices and methods. More specifically, the invention relates to intervertebral disc prostheses.

Back pain takes an enormous toll on the health and productivity of people around the world. According to the American Academy of Orthopedic Surgeons, approximately 80 percent of Americans will experience back pain at some time in their life. In just the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different intervertebral disc prostheses are currently being developed. For example, the inventors of the present invention have developed disc prostheses described in U.S. patent application Ser. Nos. 10/855,817 and 10/855,253, previously incorporated by reference. Other examples of intervertebral disc prostheses are the LINK® SB Charité disc (provided by DePuy Spine, Inc.) Mobidisk® (provided by LDR Medical (www.ldrmedical.fr)), the Bryan Cervical Disc (provided by Medtronic Sofamor Danek, Inc.), the ProDisc® or ProDisc-C® (from Synthes Stratec, Inc.), and the PCM disc (provided by Cervitech, Inc.). Although existing disc prostheses provide advantages over traditional treatment methods, improvements are ongoing.

One type of intervertebral disc prosthesis generally includes upper and lower prosthesis plates or shells, which locate against and engage the adjacent vertebral bodies, and a low friction core between the plates. In some designs, the core has upper and lower convexly curved surfaces, and the plates have corresponding, concavely curved recesses which cooperate with the curved surfaces of the core. This allows the plates to slide over the core to allow required spinal movements to take place. Some type of movement limiting structure is provided, to prevent the core from slipping out between the plates. Typically, the plates are made of one or more metals, and the core is made of a polymeric substance.

One of the challenges in designing an intervertebral disc prosthesis is to prevent or reduce wear and tear of the core. In many prosthetic discs, the plates are metallic, and the core is made of a polymeric material. Although a core made of a polymeric or other resilient material may last many years, it would be advantageous to have cores that could last even longer, so that patients (especially younger patients) would not be faced with the possibility of repeat surgeries to replace disc prostheses. At the same time, longer-lasting cores should still allow for a desirable range and ease of motion of the two vertebrae about the intervertebral disc prosthesis.

Therefore, a need exists for improved intervertebral disc prostheses. Ideally, such improved prostheses would provide improved resistance to wear and tear while also allowing a desired amount of vertebral movement about the prosthesis. At least some of these objectives will be met by the present invention.

2. Description of the Background Art

A number of exemplary intervertebral disc prostheses are listed above. Published US patent applications 2002/0035400A1 and 2002/0128715A1 describe disc implants which comprise opposing plates with a core between them over which the plates can slide. The core receives one or more central posts, which are carried by the plates and which locate in opposite ends of a central opening in the core. Such arrangements limit the load bearing area available between the plates and core.

Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558 and 6,706,068. Other patent applications related to intervertebral disc prostheses include U.S. Patent Application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, EP 1344507, EP 1344506, EP 1250898, EP 1306064, EP 1344508, EP 1344493, EP 1417940, EP 1142544, and EP 0333990.

BRIEF SUMMARY OF THE INVENTION

In one aspect of the present invention, a prosthetic disc for insertion between adjacent vertebrae includes a core having upper and lower curved surfaces and upper and lower plates. At least one of the curved surfaces of the core is composed of or covered by a metal, which forms a metallic portion of the core. Each plate has an outer surface which engages a vertebra and a metallic inner curved surface which is shaped to slide over one of the curved surfaces of the core. The center of rotation of the core is free to move relative to the upper and lower metallic plates. Thus, the plates can slide freely in all directions, not being limited to movement in a single direction as with the prior art. Metal endplates combined with a core having at least one metallic surface will help prevent wear and tear of the disc prosthesis.

"Curved surfaces" of the core and/or the plates typically means that such surfaces are spherical. However, it is also contemplated that other, non-spherical surface shapes may be used, such as but not limited to ovoid, crowned, domed or other complementary surface shapes which provide for the desired freedom of movement of the plates relative to the core. A center of rotation of the core that is free to move relative to the upper and lower plates means that the core is not fixed in an immobile state to either of the plates. Thus, the core may move laterally or "float" relative to the plates, and the plates may move freely over the core.

The upper and lower plates may be made of any suitable metal, metal alloy or combination of metals or alloys. In some embodiments, for example, the plates may be made of cobalt chrome molybdenum, titanium, stainless steel or some combination thereof. In some embodiments, titanium plates are used, and these plates may optionally include inner surfaces of titanium nitride and outer surfaces that are aluminum oxide blasted to create micro-concavities. In another embodiment, cobalt chrome plates are used, with the outer surfaces being blasted with aluminum oxide and then coated with a titanium plasma spray. In some embodiments, the plates comprise an MRI-compatible material, such as titanium, coupled with a hardened material, such as cobalt chrome molybdenum. Such materials may be coupled using any suitable means, such as welding, laminating, slip fitting, interference fitting, adhesion, welding, molding, heating and cooling one material to attach it to another, or the like. Some plates include a coating or material on the inner surfaces for reducing friction and/or wear and tear, such as a titanium nitride surface.

The metallic portion of the core may also be made of any suitable metal, alloy or combination of metals or alloys. In various embodiments, for example, one curved surface of the core, both curved surfaces of the core, or the entire core may comprise cobalt chrome molybdenum, titanium, stainless steel or some combination thereof. In some embodiments, the core and the upper and lower plates may be made of the same metal, while in alternative embodiments they may be made of different metals. In some embodiments, the core may comprise a combination of metallic and non-metallic substances, such as metal and ceramic, polymer, a combination of polymers, or the like. In such embodiments, the curved surfaces of the core may be laminated or coated in metal, or metallic curved surface portions may be attached to the non-metallic portions. In one embodiment, the core is hollow, with metallic curved surfaces.

The core may have any suitable configuration or shape. In one embodiment, the core comprises two oppositely facing, convex, low-friction, metallic or metal-covered surfaces which slidably engage the inner curved surfaces of the upper and lower plates. One or both of the upper and lower curved surfaces of the core may optionally include at least one channel on the surface(s) for allowing passage or intrusion of bodily fluid to promote lubrication between the core and at least one of the plates. In some embodiments, two or more channels are included on at least one of the core surfaces. Such channels, for example, may be oriented perpendicularly across the upper and/or lower surfaces to intersect. In some embodiments, each of the upper and lower surfaces of the core includes at least one channel. The core may have additional surface features in various embodiments, such as but not limited to threads for screwing into complementary threads on the upper and/or lower plates.

In some embodiments, the present invention further provides restraining structure on one or both of the plates or the core to hold the core against the curved surface of at least one of the plates during sliding movement of the plates over the core. For example, one or more peripheral restraining structures may be included. The peripheral restraining structure defines a limit or boundary for movement of the core relative to at least one of the upper and lower plates. Within such a peripheral boundary, however, movement of the core relative to the plate will preferably be unconstrained. That is, movement of the core relative to the plate may occur in any direction without significant inhibition or friction. The core will preferably not be attached to either the upper or lower plate, and the plates will thus be able to freely articulate relative to each other over the core, which provides a low friction bearing surface for each plate.

An advantage of the structure thus described is that the surface contact area between the core and each of the upper and lower plates may be maximized. By providing only a peripheral restraint, as opposed for example to grooves and keys on the surface of the core and plates, the width or diameter of the core relative to the size of the plate may be maximized. Moreover, the surfaces of the core and the plates which contact each other may be made smooth and free from other structure(s) that might adversely affect performance. In the preferred embodiments, both the curved surfaces of the plates and the corresponding surfaces of the core will be spherical sections. The use of spherical surfaces promotes free, unconstrained relative motion of the plates and the core in all directions.

In some embodiments, the peripheral restraining structure limits relative inclination of the plates during sliding movement of the plates over the core, usually by defining a stop structure. In other embodiments, the peripheral restraining structure lifts one side of the core relative to an opposite side of the core during sliding movement of the plates over the core. The peripheral restraining structure itself may take any of a number of different forms. In one embodiment, for example, the restraining structure comprises a ring structure on at least one of the upper and lower plates and an annular structure on at least a portion of the periphery of the core. In one embodiment, the ring structure is adapted to engage and restrain the annular structure on the core. For example, the ring structure may comprise a flange which defines an overhang over at least a portion of the periphery of one of the plates. The overhang of the flange will receive the annular structure on the core to provide an interference fit which retains the core against the curved surface of the plate but allows the core to slide freely and in an unconstrained manner within the limit or boundary defined by the flange. The annular structure on the core may be a rim which extends continuously or discontinuously (preferably continuously) around a lateral circumference of the core. By providing a rim which has a width, usually a diameter, which is slightly greater than the corresponding width of an inner edge of the flange at one point, the core will be held in place and will not be dislodged from the cavity defined by the ring structure in normal use.

In an alternative embodiment, the annular structure on the core may have a width or outer diameter that is slightly smaller than an inner diameter of the ring structure (such as a flange) on the upper or lower plate. Thus, the annular structure on the core may be passed through the ring structure to engage the core with the upper or lower plate. The core is then held in place, relative to the upper or lower plate, via forces applied by the adjacent vertebrae and surrounding soft tissue structures. Essentially, this embodiment is analogous to a ball-and-socket joint. Such an embodiment may be advantageous for ease of assembly of prosthetic disc with a metallic core and metallic endplates.

Usually, the flange or other ring structure as well as the rim or other annular structure will be formed continuously about the periphery of the plate and core, respectively. Alternatively, however, either or both of the annular structure and the ring structure could be formed discontinuously. That is, so long as at least some portion of the ring structure and the annular structure remain engaged during all expected geometries and uses of the prosthetic disc, the objective of holding the core against the curved surface of the plate will be met.

Optionally, in some embodiments the outer surfaces of the upper and lower plates have at least one surface feature for promoting attachment of the outer surfaces to the vertebrae. For example, such surface features may include a plurality of serrations disposed along the outer surfaces. Some embodiments include additional or alternative features on the outer surfaces for enhancing attachment of the prosthesis to vertebral bone, such as a material or coating, like a titanium plasma spray. Multiple micro-concavities may be formed on the outer surfaces, for example by aluminum oxide spraying, to further enhance attachment. Additionally or alternatively, the surface features may include at least one fin disposed on each of the outer surfaces. In some embodiments, the fin includes at least one hole for further promoting attachment to the vertebrae. Fins may extend vertically from their corresponding outer surfaces at right angles, or alternatively the fins may extend from their corresponding outer surface at angles other than 90°. Fins may also have any suitable orientation relative to the anterior-posterior axis of the prosthesis. For example, a fin may extend in a straight line from anterior to posterior, without being angled. Alternatively, the fin may be rotated or angled away from the anterior-posterior axis at any suitable angle between 0° and 180°. In one embodiment, each fin is disposed in a lateral orientation on the outer surfaces.

In another aspect of the present invention, a prosthetic disc for insertion between adjacent vertebrae includes a core having upper and lower curved surfaces, and upper and lower plates. Again, at least one of the curved surfaces of the core is composed of a metal, and in some embodiments the entire core is metallic. Additionally, each of the curved surfaces includes at least one surface channel for allowing passage of bodily fluid to promote lubrication between the core and the plates. Each plate has an outer surface which engages a vertebra and a metallic inner curved surface which is shaped to slide over one of the curved surfaces of the core. In a preferred embodiment, the center of rotation of the core is free to move relative to the upper and lower metallic plates. Any of the features described above may also be incorporated in various embodiments.

In another aspect of the present invention, a prosthetic disc for insertion between adjacent vertebrae includes a metallic core having upper and lower curved surfaces and upper and lower metallic plates. Each plate has an outer surface which engages a vertebra and an inner curved surface which slides over the curved surface of the core. The center of rotation of the core is free to move relative to the upper and lower metallic plates. In some embodiments, the core and the plates are made of the same metal. Some embodiments further include one or more channels on each curved surface of the core, on one or more of the plates, or both, for promoting lubrication.

In another aspect of the present invention, a method for assembling a prosthetic disc for insertion between adjacent vertebrae involves movably coupling a core with a first metallic endplate to form an interference fit between the core and the first endplate and contacting the core with a second metallic endplate. At least one of the curved surfaces of the core is metallic, as described above. In some embodiments, coupling the metallic core with the first metallic endplate involves heating the first endplate sufficiently to cause it to expand, inserting a portion of the core into the expanded endplate restraining structure, and allowing the first endplate to cool, thus contracting to form the interference fit around the portion of the core. In an alternative embodiment, coupling the core with the first endplate comprises forming the endplate around the core. Alternatively, coupling the core with the first endplate may involve screwing the core into the first endplate via complementary threads on the core and the first endplate. In some embodiments, coupling the core with the first endplate may involve engaging a peripheral protrusion of the core with a peripheral restraining structure of the first endplate.

In another aspect of the present invention, a method for implanting an intervertebral disc prosthesis between adjacent vertebrae comprises implanting an upper metallic plate against a lower surface of an upper vertebral body, implanting a lower metallic plate against an upper surface of a lower vertebral body, and disposing a core (at least one curved surface of which is metallic) between the upper and lower plates. The core floats with a mobile center of rotation between spherical cavities in each of the upper and lower plates. In some embodiments, the plates restrain peripheral movement of the core using at least one peripheral restraining member. In some embodiments, disposing the core between the plates involves passing an annular structure of the core through a ring structure of one of the plates. In some embodiments, implanting each of the plates comprises sliding a fin on each plate into a corresponding groove formed in its respective vertebral body. The fin may slide into the groove in any suitable direction, such as posterior-anterior, anterior-posterior, lateral, or any angled direction between an anterior-posterior orientation and a lateral orientation. Optionally, implanting may further involve contacting textured outer surfaces of the upper and lower plates with the upper and lower surfaces of the vertebral bodies.

These and other aspects and embodiments will be described in further detail below, with reference to the drawing figures.

BRIEF DESCRIPTION OF THE DRAWINGS

FIGS. 1 and 1A ae cross-sectional anterior views of a prosthetic disc with the prosthesis plates and core in vertical alignment, according to embodiments of the present invention;

FIG. 2 is a side view of the prosthetic disc in FIG. 1 after sliding movement of the plates over the core;

DETAILED DESCRIPTION OF THE INVENTION

Figure 1A:
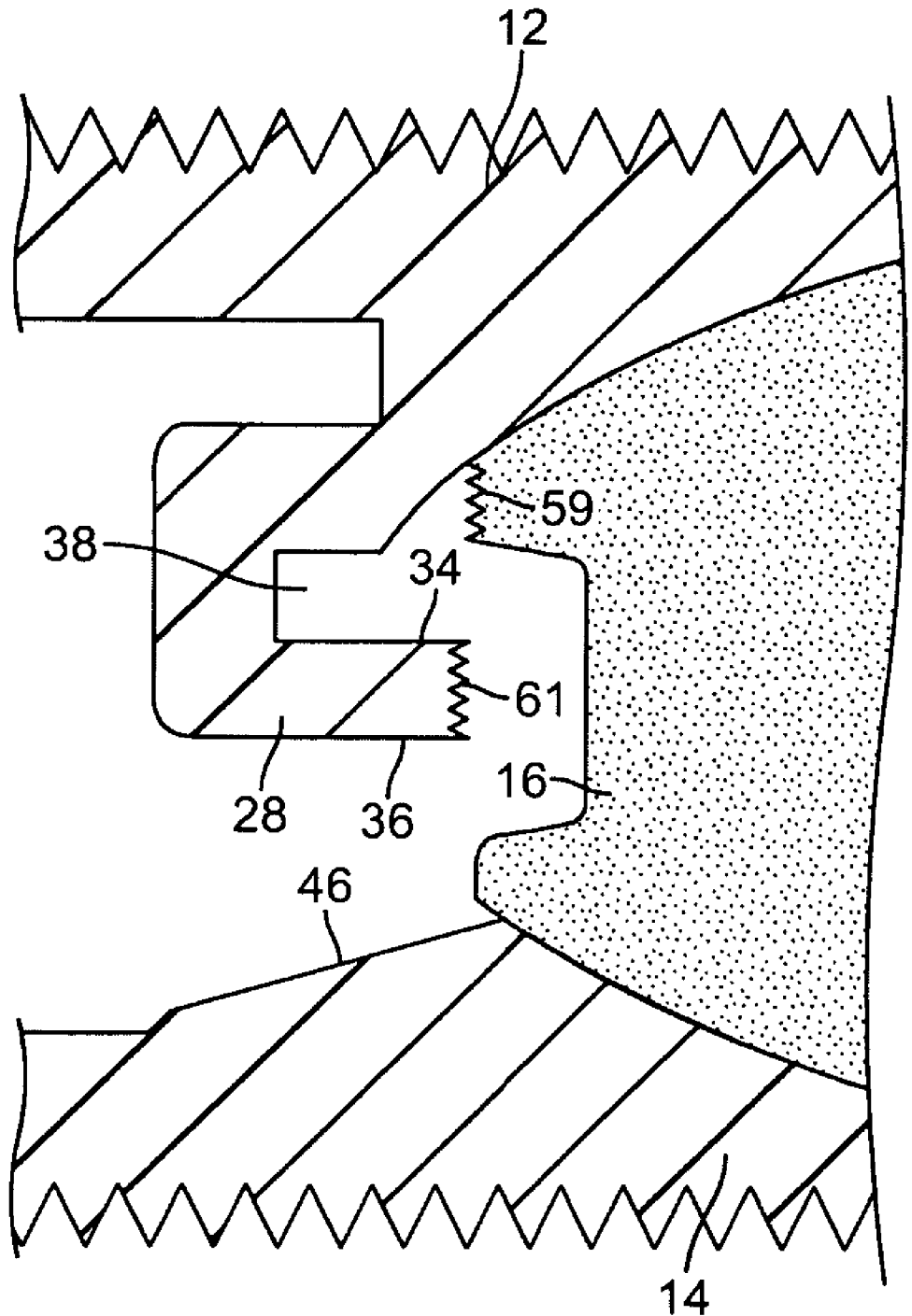

Various embodiments of the present invention generally provide for an intervertebral disc prosthesis having upper and lower plates and a core having at least one metallic surface. In various embodiments, the core may have a mobile center of rotation, one or more surface channels for promoting passage of lubricating fluid, or both. FIGS. 1-6 generally demonstrate one embodiment of such a prosthesis. The general principles of the present invention, however, may be applied to any of a number of other disc prostheses, such as but not limited to the LINK® SB Charité disc (provided by DePuy Spine, Inc.) Mobidisk® (provided by LDR Medical (www.ldrmedical.fr)), the Bryan Cervical Disc (provided by Medtronic Sofamor Danek, Inc.), the ProDisc® or ProDisc-C® (from Synthes Stratec, Inc.), and the PCM disc (provided by Cervitech, Inc.).

That being said, and with reference now to FIGS. 1-4 a prosthetic disc 10 for intervertebral insertion between two adjacent spinal vertebrae (not shown) suitably includes an upper plate 12, a lower plate 14 and a core 16 located between the plates. The upper plate 12 includes an outer surface 18 and an inner surface 24 and may be constructed from any suitable metal, alloy or combination of metals or alloys, such as but not limited to cobalt chrome molybdenum, titanium (such as grade 5 titanium), stainless steel and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In other cervical and lumbar disc embodiments, any other suitable metals or combinations of metals may be used. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. Any suitable technique may be used to couple materials together, such as snap fitting, slip fitting, lamination, interference fitting, use of adhesives, welding and/or the like. Any other suitable combination of materials and coatings may be employed in various embodiments of the invention.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have serrations 20 or other surface features for promoting adhesion of the upper plate 12 to a vertebra. In the embodiment shown (seen best in FIG. 6), the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

The outer surface 18 may also carry an upstanding, vertical fin 22 extending in an anterior-posterior direction. The fin 22 is pierced by transverse holes 23. In alternative embodiments, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90°. Furthermore, multiple fins 22 may be attached to the surface 18 and/or the fin 22 may have any other suitable configuration, in various embodiments. In other embodiments, the fin 22 In some embodiments, such as discs 10 for cervical insertion, the fins 22, 42 may be omitted altogether.

The inner, spherically curved concave surface 24 is formed at a central (from right to left), axial position with a circular recess 26 as illustrated. At the outer edge of the curved surface 24, the upper plate 12 carries peripheral restraining structure comprising an integral ring structure 26 including an inwardly directed rib or flange 28. The flange 28 forms part of a U-shaped member 30 joined to the major part of the plate by an annular web 32. The flange 28 has an inwardly tapering shape and defines upper and lower surfaces 34 and 36 respectively which are inclined slightly relative to the horizontal when the upper plate 12 is at the orientation seen in FIG. 1. An overhang 38 of the U-shaped member 30 has a vertical dimension that tapers inwardly as illustrated.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

At the outer edge of the inner curved surface 44, the lower plate 14 is provided with an inclined ledge formation 46. Alternatively, the lower plate 14 may include peripheral restraining structure analogous to the peripheral restraining structure 26 on the upper plate 12.

The core 16 of the disc 10 is at least partially made of one or more metals, alloys or a combination of metals or alloys. For example, metals used to form all or part of the core 16 may include but are not limited to cobalt chrome molybdenum, titanium (such as grade 5 titanium), stainless steel and/or the like. In some embodiments, the core 16 may be made of the same material as the upper plate 12 and the lower plate 14, which may help resist oxidation of metallic surfaces of the disc 10. In alternative embodiments, the core 16 may be made of different material(s) than the plates 12, 14. In the embodiment shown, the core 16 has identical upper and lower spherically curved convex surfaces 48, 50. At least one of the curved surfaces 48, 50 is metallic or covered in metal. In some embodiments, the entire core 16 is metallic, while in other embodiments the curved surfaces 48, 50 may be coated or laminated with metal, or one or more metallic surfaces may be otherwise attached to the core 16. In some embodiments, the core 16 is made of a polymer or ceramic, with attached metallic curved surfaces 48, 50. Alternatively, the core 16 may be a hollow metallic structure. The radius of curvature of these surfaces matches the radius of curvature of the inner surfaces 24, 44 of the upper and lower plates 12, 14. The curved surfaces are accordingly complementary.

The core 16 is symmetrical about a central, equatorial plane 52 which bisects it laterally. (Although in other embodiments, the core 16 may be asymmetrical.) Lying on this equatorial plane is an annular recess or groove 54 which extends about the periphery of the core. The groove 54 is defined between upper and lower ribs or lips 56. When the plates 12, 14 and core 16 are assembled and in the orientation seen in FIG. 1, the flange 28 lies on the equatorial plane and directly aligned with the groove 54. The outer diameter 58 of the lips 56 is preferably very slightly larger than the diameter 60 defined by the inner edge of the flange 28. In some embodiments, the core 16 is movably fitted into the upper plate 12 via an interference fit. To form such an interference fit with a metal core 16 and metal plate 12, any suitable techniques may be used. For example, the plate 12 may be heated so that it expands, and the core 16 may be dropped into the plate 12 in the expanded state. When the plate 12 cools and contracts, the interference fit is created. In another embodiment, the upper plate 12 may be formed around the core 16. Alternatively, the core 16 and upper plate 12 may include complementary threads 59, 61 as shown in FIG. 1A, which allow the core 16 to be screwed into the upper plate 12, where it can then freely move.

In an alternative embodiment (not shown), the outer diameter 58 of the lips 56 may be very slightly smaller than the diameter 60 defined by the inner edge of the flange 28. In such embodiments, the core 16 and the plates 12, 14 are not coupled via an interference fit but are instead coupled via forces applied by the vertebral column itself, thus acting analogously to a ball-and-socket joint.

Figure 5:
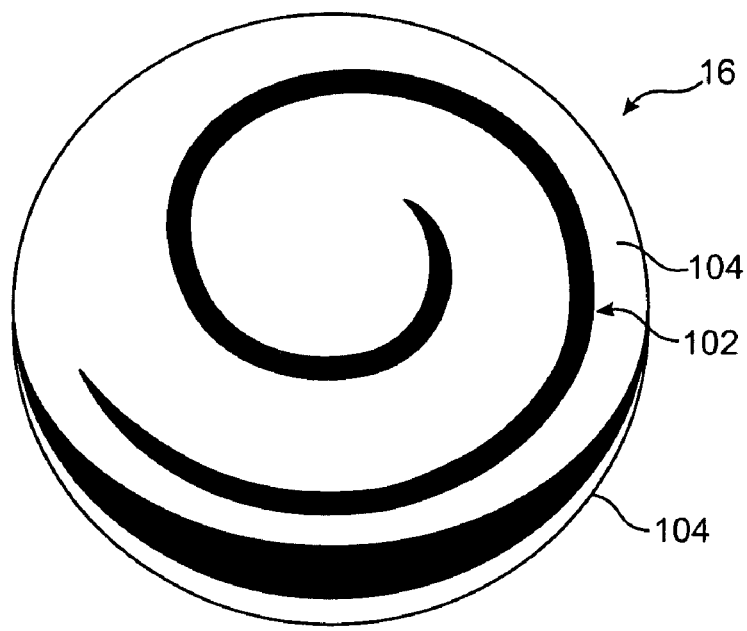
FIG. 5 is a perspective view of a core of a prosthetic disc, according to one embodiment of the present invention.
Figure 6:
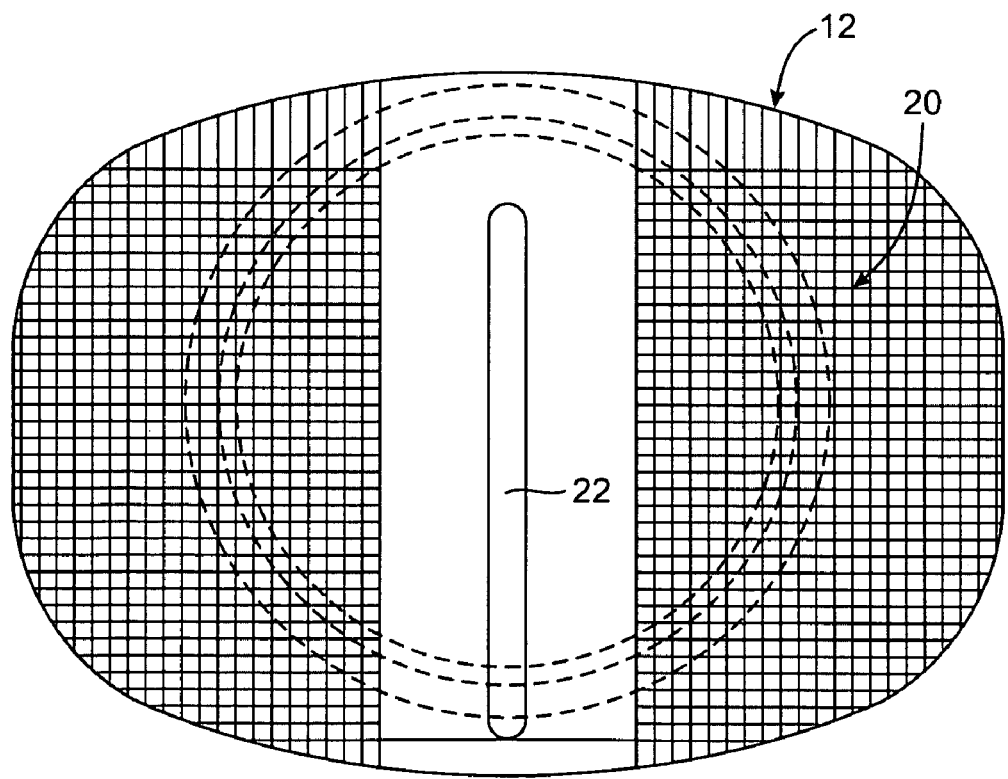
FIG. 6 is a superior view of an upper plate of a prosthetic disc, according to one embodiment of the present invention.

Referring now to FIG. 5, in some embodiments, the core 16 includes one or more surface channels 102 for allowing passage of fluid along the contact surfaces 104 of the core 16. Bodily fluids and/or injected fluid may pass through such a channel 102, between the core 16 and the upper and lower plates 12, 14, to promote lubrication between the contact surfaces 104 of the core and their corresponding surfaces on the upper and lower plates 12, 14. Any number, pattern, shape, depth, width or length of surface channels 102 may be included on a contact surface 104, in various embodiments. In some embodiments, for example, channels 102 may have a depth of about 3 mm or less, and more preferably about 2 mm or less, and even more preferably about 1 mm or less. Surface channels 102 may have a cross-sectional shape that is curved, rectangular, V-shaped or any other suitable shaped. Furthermore, surface channels 102 may be disposed on the contact surface(s) 104 of the core 16 in a helical pattern (as shown) or in any other suitable pattern, such as circular, rectangular, curved, one or more straight, parallel lines, two or more perpendicular lines, or the like. Surface channels 102 help prevent sticking or loss of freedom of motion (seizing) between the core 16 and the plates 12, 14 which may occur otherwise due to metal-on-metal contact.

In some embodiments, one or both of the inner surfaces 24, 44 of the upper and lower plates 12, 14 may also include one or more surface channels 25, 45 as shown in FIG. 1. Again, such channels may have any suitable configuration, size, number and shape, and may assist in promoting lubrication between the core 16 and the upper and lower plates 12, 14.

Figure 4:
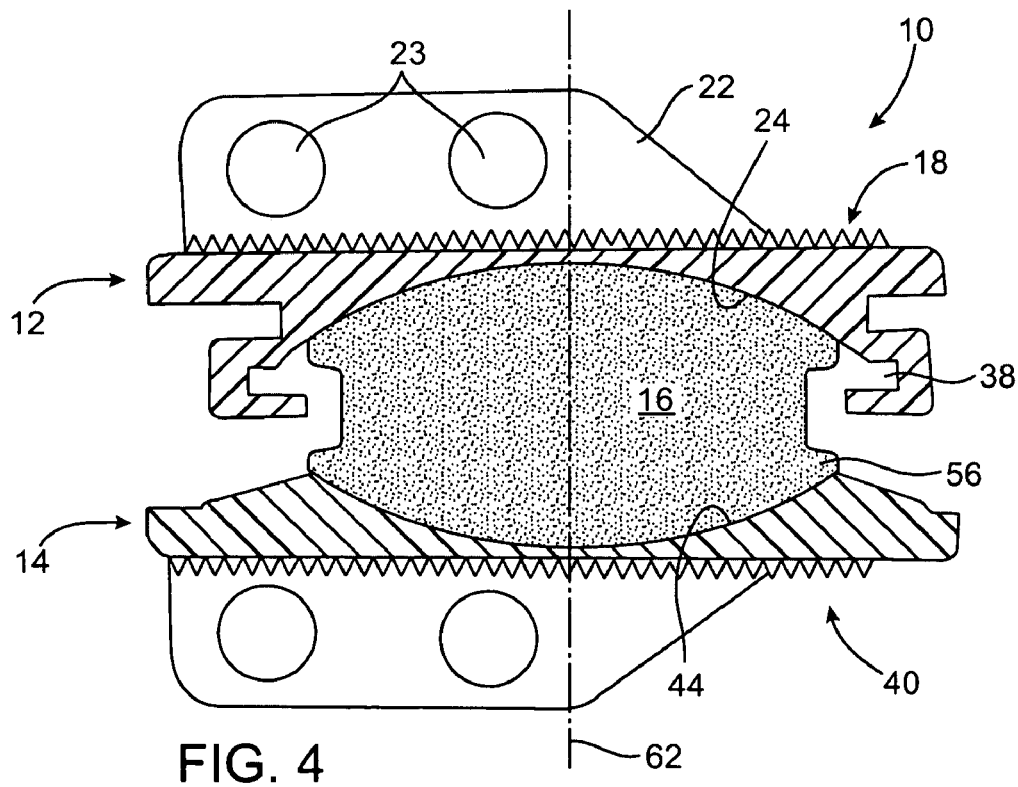
FIG. 4 is a side view of the prosthetic disc in FIG. 1 with the prosthesis plates and core in vertical alignment.

The central axis of the disc 10 (the axis passing through the centers of curvature of the curved surfaces) is indicated with the reference numeral 62. As shown in FIG. 1, the disc 10 may be symmetrical about a central anterior-posterior plane containing the axis 62. Referring to FIG. 4, in some embodiments the axis 62 is posteriorly disposed, i.e. is located closer to the posterior limit of the disc than the anterior limit thereof.

In use, the disc 10 is surgically implanted between adjacent spinal vertebrae in place of a damaged disc. The adjacent vertebrae are forcibly separated from one another to provide the necessary space for insertion. The disc is inserted, normally in a posterior direction, into place between the vertebrae with the fins 22, 42 of the plates 12, 14 entering slots cut in the opposing vertebral surfaces to receive them. During and/or after insertion, the vertebrae, facets, adjacent ligaments and soft tissues are allowed to move together to hold the disc in place. The serrated and microfinished surfaces 18, 40 of the plates 12, 14 locate against the opposing vertebrae. The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

In the assembled disc 10, the complementary and cooperating spherical surfaces of the plates and core allow the plates to slide or articulate over the core through a fairly large range of angles and in all directions or degrees of freedom, including rotation about the central axis 62. FIGS. 1 and 4 show the disc 10 with the plates 12 and 14 and core 16 aligned vertically with one another on the axis 62. FIG. 2 illustrates a situation where maximum anterior flexion of the disc 10 has taken place. At this position, the upper rib 56 has entered the hollow 38 of the U-shaped member 30, the lower surface of the rib 56 has moved into contact with the upper surface 34 of the flange 28, the flange having moved into the groove 54, and the lower surface 36 of the flange has moved into contact with the upper surface of the ledge formation 46, as will be seen in the encircled areas 69. Abutment between the various surfaces prevents further anterior flexure. The design also allows for the inner extremity of the flange 28 to abut against the base of the groove 54, thereby limiting further relative movement between the core and plate. A similar configuration is achieved in the event of maximum posterior flexure of the plates 12, 14 over the core, such as during spinal extension and/or in the event of maximum lateral flexure.

Figure 3:
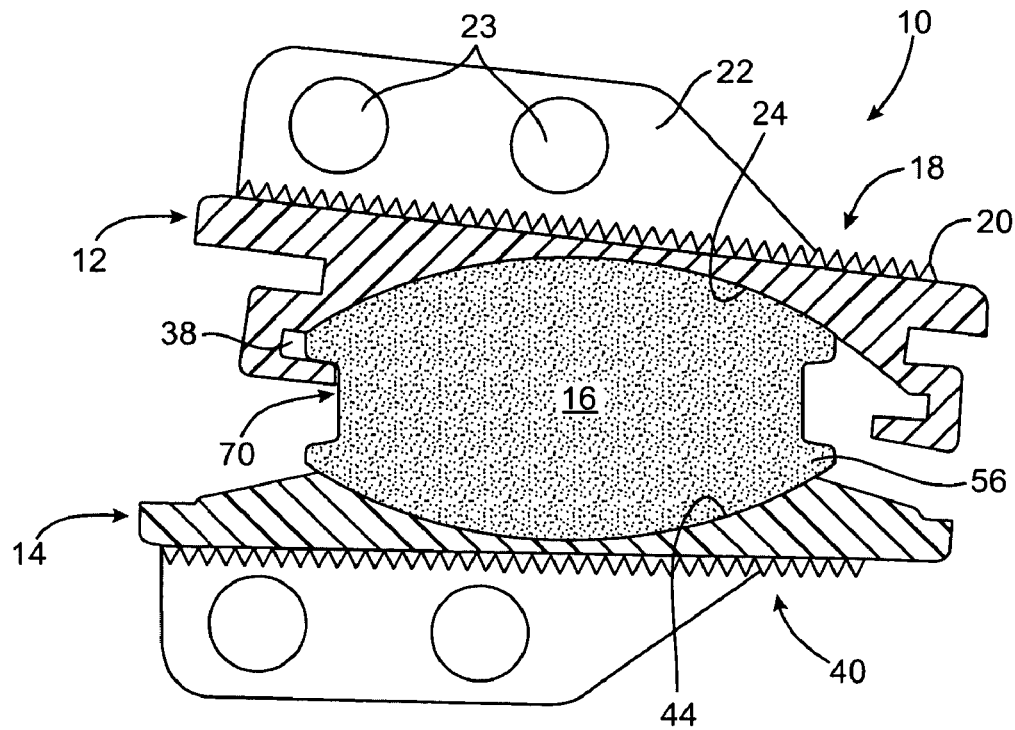
FIG. 3 is a side view of the prosthetic disc in FIG. 1 after translational movement of the plates relative to the core.

FIG. 3 illustrates how the disc 10 can also allow for translational movement of the plates relative to the core. In the illustrated situation there has been lateral translation of the plates relative to the core. The limit of lateral translation is reached when the inner extremity of the flange 28 abuts the base of the groove 54 as indicated by the numeral 70.

The flange 28 and the groove 54 defined between the ribs 56, prevent separation of the core from the plates. In other words, the cooperation of the retaining formations ensures that the core is held captive between the plates at all times during flexure of the disc 10.

In an alternative embodiment, the continuous annular flange 28 may be replaced by a retaining formation comprising a number of flange segments which are spaced apart circumferentially. Such an embodiment could include a single, continuous groove 54 as in the illustrated embodiment. Alternatively, a corresponding number of groove-like recesses spaced apart around the periphery of the core could be used, with each flange segment opposing one of the recesses. In another embodiment, the continuous flange or the plurality of flange segments could be replaced by inwardly directed pegs or pins carried by the upper plate 12. This embodiment could include a single, continuous groove 54 or a series of circumferentially spaced recesses with each pin or peg opposing a recess.

In yet another embodiment, the retaining formation(s) could be carried by the lower plate 14 instead of the upper plate, i.e. the plates are reversed. In some embodiments, the upper (or lower) plate is formed with an inwardly facing groove, or circumferentially spaced groove segments, at the edge of its inner, curved surface, and the outer periphery of the core is formed with an outwardly facing flange or with circumferentially spaced flange segments.

Although the foregoing is a complete and accurate description of the invention, any of a number of modifications, additions or the like may be made to the various embodiments without departing from the scope of the invention. Therefore, nothing described above should be interpreted as limiting the scope of the invention at it is described in the claims.

What is claimed is:

1. A prosthetic disc for insertion between adjacent vertebrae, the prosthetic disc comprising:
   a core having upper and lower curved surfaces, wherein each of the curved surfaces comprises a metal;
   upper and lower plates, each plate having an outer surface which engages a vertebra and a metallic inner curved surface which is shaped to slide and translate over one of the curved metallic surfaces of the core, wherein a center of rotation of the core is free to move relative to the upper and lower plates;
   a peripheral restraining structure on at least one of the upper plate and the lower plate to hold the core against a curved surface of at least one of the plates during sliding movement of the plates over the core, the peripheral restraining structure comprising an annular structure extending over at least a portion of the periphery of the core and a ring structure on one of the upper and lower plates, which ring structure engages and retains the annular structure,
   wherein the restraining structure is adapted to contact an opposing plate to limit relative inclination of the plates during sliding movement of the plates over the core.

2. A prosthetic disc as in claim 1, wherein the plates comprise at least one metal selected from the group consisting of cobalt chrome molybdenum, titanium and stainless steel.

3. A prosthetic disc as in claim 2, wherein each plate comprises an MRI compatible material coupled with a hardened material forming the inner surface.

4. A prosthetic disc as in claim 3, wherein the MRI-compatible material comprises titanium and the hardened material comprises cobalt chrome molybdenum.

5. A prosthetic disc as in claim 3, wherein the MRJ-compatible material comprises titanium and the hardened material comprises titanium nitride.

6. A prosthetic disc as in claim 3, wherein the MM-compatible material and the hardened material are coupled together using a process selected from the group consisting of welding, lamination, slip fitting, interference fitting, adhesion and heating and cooling one material to attach it to another.

7. A prosthetic disc as in claim 1, wherein at least one curved surface of the core comprises at least one metal selected from the group consisting of cobalt chrome molybdenum, titanium and stainless steel.

8. A prosthetic disc as in claim 7, wherein the entire core is metallic.

9. A prosthetic disc as in claim 8, wherein the core and both plates comprise the same metal.

10. A prosthetic disc as in claim 7, wherein a portion of the core between the curved surfaces comprises ceramic.

11. A prosthetic disc as in claim 7, wherein a portion of the core between the curved surfaces comprises a polymer.

12. A prosthetic disc as in claim 1, wherein the core comprises two oppositely facing convex low-friction surfaces which slidably engage the inner curved surfaces of the upper and lower plates.

13. A prosthetic disc as in claim 1, wherein at least one of the curved surfaces is spherical.

14. A prosthetic disc as in claim 13, wherein both curved surfaces are spherical.

15. A prosthetic disc as in claim 1, further including at least one surface channel on at least one of the upper and lower curved surfaces of the core for allowing passage of bodily fluid to promote lubrication between the core and at least one of the plates.

16. A prosthetic disc as in claim 15, wherein the at least one surface channel comprises a helical channel.

17. A prosthetic disc as in claim 15, wherein the at least one surface channel comprises two perpendicular channels.

18. A prosthetic disc as in claim 15, wherein each of the upper and lower surfaces of the core includes at least one surface channel.

19. A prosthetic disc as in claim 1 or 15, further including at least one surface channel on at least one of the inner curved surfaces of the plates.

20. A prosthetic disc as in claim 19, wherein each of the inner curved surfaces of the plates includes at least one surface channel.

21. A prosthetic disc as in claim 1, wherein at least one of the upper and lower curved surfaces of the core includes threads for movably coupling the core with at least one of the upper and lower plates via complementary threads thereon.

22. A prosthetic disc as in claim 1, wherein movement of the core within the restraining structure is unconstrained.

23. A prosthetic disc as in claim 1, wherein the peripheral restraining structure defines a stop structure to limit relative inclination of the plates during sliding movement of the plates over the core.

24. A prosthetic disc as in claim 1, wherein the peripheral restraining structure defines a stop structure to limit axial rotation of the plates during sliding movement of the plates over the core.

25. A prosthetic disc as in claim 1, wherein the peripheral restraining structure will engage one side of the core to lift an opposite side of the core during sliding movement of the plates over the core.

26. A prosthetic disc as in claim 1, wherein the ring structure comprises a flange which defines an overhang, and wherein at least part of the annular structure on the core extends into the overhang to provide an interference fit of the core with the flange.

27. A prosthetic disc as in claim 26, wherein the annular structure comprises a rim which extends continuously around a lateral circumference of the core, the rim having a greater width at least some locations than a width of an inner edge of the flange to provide said interference fit.

28. A prosthetic disc as in claim 1, wherein the outer surfaces of the upper and lower plates have at least one surface feature for promoting attachment of the outer surfaces to the vertebrae.

29. A prosthetic disc as in claim 28, wherein the at least one surface feature comprises a plurality of serrations disposed along the outer surfaces.

30. A prosthetic disc as in claim 29, wherein the at least one surface feature further comprises a surface coating.

31. A prosthetic disc as in claim 30, wherein the surface coating comprises plasma sprayed titanium.

32. A prosthetic disc as in claim 29, wherein the at least one surface feature further comprises a plurality of concavities formed by aluminum oxide blasting.

33. A prosthetic disc as in claim 29, wherein the at least one surface feature further comprises at least one fin disposed on each of the outer surfaces.

34. A prosthetic disc as in claim 1, wherein the core has a height between the upper and lower curved surfaces and a width, and wherein a core maximum height is smaller than the core width.

35. A prosthetic disc for insertion between adjacent vertebrae, the prosthetic disc comprising:
   a core having upper and lower curved surfaces, wherein each of the curved surfaces comprises a metal;
   upper and lower plates, each plate having an outer surface which engages a vertebra and a metallic inner curved surface which is shaped to slide and translate over one of the curved metallic surfaces of the core, wherein a center of rotation of the core is free to move relative to the upper and lower plates; and
   a peripheral restraining structure on at least one of the upper plate and the lower plate to hold the core against a curved surface of at least one of the plates during sliding movement of the plates over the core, wherein the restraining structure is adapted to contact an opposing plate to limit relative inclination of the plates during sliding movement of the plates over the core;
   wherein the peripheral restraining structure comprises:
      an annular structure extending over at least a portion of the periphery of the core, and
      a ring structure on one of the upper and lower plates, wherein the annular structure has a diameter sized to pass through the ring structure, and wherein the core is retained within the ring structure due to forces placed on the prosthetic disc via the adjacent vertebrae.

36. A prosthetic disc for insertion between adjacent vertebrae, the prosthetic disc comprising:
   a core having upper and lower curved surfaces, wherein each of the curved surfaces comprises a metal;
   upper and lower plates, each plate having an outer surface which engages a vertebra and a metallic inner curved surface which is shaped to slide and translate over one of the curved metallic surfaces of the core, wherein a center of rotation of the core is free to move relative to the upper and lower plates; and
   a peripheral restraining structure on at least one of the upper plate and the lower plate to hold the core against a curved surface of at least one of the plates during sliding movement of the plates over the core, wherein the restraining structure is adapted to contact an opposing plate to limit relative inclination of the plates during sliding movement of the plates over the core;
   wherein the peripheral restraining structure comprises:
      a groove around a lateral edge of the core; and
      a ring structure on at least one of the upper and lower plates, said ring structure having a lip which engages the groove.

37. A prosthetic disc as in claim 36, wherein the lip extends into the groove to form an interference fit between the ring structure and the core.

38. A prosthetic disc for insertion between adjacent vertebrae, the prosthetic disc comprising:
   a metallic core having upper and lower curved metallic spherical surfaces;
   first and second metallic plates, each plate having an outer surface which engages a vertebra and an inner curved spherical surface which slides and translates over the curved spherical surface of the core, wherein a center of rotation of the core is free to move relative to the upper and lower metallic plates; and
   a peripheral restraining structure on at least one of the first and second plates to hold the core against a curved surface of at least one of the plates during sliding movement of the plates over the core, the peripheral restraining structure comprising a peripheral structure extending over at least a portion of the periphery of the core and a projecting structure on one of the first and second plates, which projecting structure engages and retains the peripheral structure,
   wherein the restraining structure is adapted to contact an opposing plate to limit relative inclination of the plates during sliding movement of the plates over the core.

39. A prosthetic disc as in claim 38, further including at least one surface channel on each of the upper and lower curved surfaces of the core for promoting flow of lubricating fluid between the core and the plates.

40. A prosthetic disc as in claim 39, further including at least one surface channel on each of the inner curved surfaces of the first and second plates for promoting flow of lubricating fluid between the core and the plates.

41. A prosthetic disc as in claim 38, wherein the core and the plates comprise at least one metal selected from the group consisting of cobalt chrome molybdenum, titanium and stainless steel.

42. A prosthetic disc as in claim 41, wherein the core and the plates comprise the same metal.

43. A prosthetic disc as in claim 38, wherein the core has a height between the upper and lower curved surfaces and a width, and wherein a core maximum height is smaller than the core width.

44. A prosthetic disc as in claim 38, wherein the projecting structure comprises an inwardly projecting ring.

45. A method for implanting an intervertebral disc prosthesis between adjacent vertebrae, the method comprising:
   implanting an upper metallic plate against a lower surface of an upper vertebral body;
   implanting a lower metallic plate against an upper surface of a lower vertebral body;
   disposing a core between the upper and lower plates, the core having curved surface comprising a metal, wherein disposing the core between the plates comprises passing an annular structure on the core through a ring structure on at least one of the plates, and wherein the annular structure has a diameter sized to pass through the ring structure to restrain peripheral movement of the core; and
   allowing the core to float with a mobile center of rotation between spherical cavities in each of the upper and lower plates.

46. A method as in claim 45, wherein implanting each of the plates comprises sliding a fin on each plate into a corresponding groove formed in its respective vertebral body.

47. A method as in claim 46, wherein sliding the fin is performed in a direction from posterior to anterior.

48. A method as in claim 46, wherein sliding the fin is performed in a lateral direction.

49. A method as in claim 46, wherein sliding the fin is performed in angled direction between posterior-anterior and lateral.

50. A method as in claim 46, wherein implanting further comprises contacting textured outer surfaces of the upper and lower plates with the upper and lower surfaces of the vertebral bodies.

51. A method as in claim 45, wherein the core has a height between the upper and lower curved surfaces and a width, and wherein a core maximum height is smaller than the core width.

52. A prosthetic disc for insertion between adjacent vertebrae, the prosthetic disc comprising:
   a core having upper and lower bearing surfaces, wherein each of the bearing surfaces comprises a metal;
   upper and lower plates, each plate having an outer surface which engages a vertebra and a metallic inner bearing surface which is shaped to slide and translate over one of the bearing metallic surfaces of the core, wherein a center of rotation of the core is free to move relative to the upper and lower plates;
   a peripheral restraining structure on at least one of the upper plate and the lower plate to hold the core against a bearing surface of at least one of the plates during sliding movement of the plates over the core, the peripheral restraining structure comprising an annular structure extending over at least a portion of the periphery of the core and a ring structure on one of the upper and lower plates, which ring structure engages and retains the annular structure,
   wherein the restraining structure is adapted to contact an opposing plate to limit relative inclination of the plates during sliding movement of the plates over the core.

53. A prosthetic disc as in claim 52, wherein at least one bearing surface of the core comprises at least one metal selected from the group consisting of cobalt chrome molybdenum, titanium and stainless steel.

54. A prosthetic disc as in claim 53, wherein the entire core is metallic.

55. A prosthetic disc as in claim 54, wherein the core and both plates comprise the same metal.

56. A prosthetic disc as in claim 52, wherein the core comprises two oppositely facing convex low-friction surfaces which slidably engage the inner bearing surfaces of the upper and lower plates.

57. A prosthetic disc as in claim 52, wherein at least one of the bearing surfaces of the core is spherical.

58. A prosthetic disc as in claim 52, wherein both bearing surfaces of the core are spherical.

59. A prosthetic disc as in claim 52, wherein at least one of the upper and lower bearing surfaces of the core includes threads for movably coupling the core with at least one of the upper and lower plates via complementary threads thereon.

60. A prosthetic disc as in claim 52, wherein movement of the core within the restraining structure is unconstrained.

61. A prosthetic disc as in claim 52, wherein the peripheral restraining structure defines a stop structure to limit axial rotation of the plates during sliding movement of the plates over the core.

62. A prosthetic disc as in claim 52, wherein the peripheral restraining structure will engage one side of the core to lift an opposite side of the core during sliding movement of the plates over the core.

63. A prosthetic disc as in claim 52, wherein the ring structure comprises a flange which defines an overhang, and wherein at least part of the annular structure on the core extends into the overhang to provide an interference fit of the core with the flange.

64. A prosthetic disc as in claim 63, wherein the annular structure comprises a rim which extends continuously around a lateral circumference of the core, the rim having a greater width at least some locations than a width of an inner edge of the flange to provide said interference fit.

* * * * *

UNITED STATES PATENT AND TRADEMARK OFFICE
CERTIFICATE OF CORRECTION

PATENT NO. : 7,575,599 B2  
APPLICATION NO. : 10/903913  
DATED : August 18, 2009  
INVENTOR(S) : Villiers et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this

Seventh Day of September, 2010

David J. Kappos  
*Director of the United States Patent and Trademark Office*